United States Patent [19]
Nitecki et al.

[11] Patent Number: 6,073,483
[45] Date of Patent: Jun. 13, 2000

[54] DEVICE FOR MEASURING THE VISCOSITY OF A FLUID

[75] Inventors: Jean-Pierre Nitecki, Buc; Patrick Siri, Abbeville, both of France

[73] Assignee: Schlumberger Systémes, Montrouge, France

[21] Appl. No.: 09/201,584

[22] Filed: Nov. 30, 1998

[30] Foreign Application Priority Data

Nov. 28, 1997 [FR] France .................................. 97 15042

[51] Int. Cl.$^7$ .............................. G01N 11/04; G01F 7/00; G01F 1/37
[52] U.S. Cl. .......................... 73/54.05; 73/196; 73/861.52
[58] Field of Search .................. 73/54.01, 54.13, 73/54.05, 54.06, 54.02, 54.09, 861, 861.19, 195, 196, 197, 198, 861.52, 54.04

[56] References Cited

U.S. PATENT DOCUMENTS

| | | | |
|---|---|---|---|
| 4,384,472 | 5/1983 | Tournier . | |
| 4,961,344 | 10/1990 | Rodder | 73/861.52 X |
| 5,056,357 | 10/1991 | Dymling et al. . | |
| 5,172,585 | 12/1992 | Gleissle . | |
| 5,359,881 | 11/1994 | Kalotay et al. | 73/54.06 |
| 5,447,440 | 9/1995 | Davis et al. . | |
| 5,661,232 | 8/1997 | Van Cleve et al. . | |
| 5,861,566 | 1/1999 | Van Cleve et al. | 73/861.52 |

OTHER PUBLICATIONS

Patent Abstracts of Japan, vol. 095, No. 008, Sep. 29, 1995, & JP 07 128211 A (Dainippon Ink & Chem. Inc.) May 19, 1995.

Kalotay P., et al., "On–Line Viscosity Measurement with Coriolis Mass Flow Meters", Advances in Instrumentation and Control, vol. 46, No. Part 2, Jan. 1, 1991, pp. 1029–1039, XP000347545.

*Primary Examiner*—Hezron Williams
*Assistant Examiner*—Jay L. Politzer
*Attorney, Agent, or Firm*—Frishauf, Holtz, Goodman, Langer & Chick, P.C.

[57] ABSTRACT

A device for measuring the viscosity of a fluid includes a viscosensitive unit through which the fluid flows under laminar flow conditions, a first turbulent flow flowmeter in series with the viscosensitive unit, and a second turbulent flow flowmeter shunting at least the viscosensitive unit. The flowmeters are adapted to determine the head loss $\Delta p$ and the flowrate q of the fluid through the viscosensitive unit, the dynamic viscosity $\mu$ being given by the equation $\mu = \Delta p / kq$ where k is a constant dependent on the viscosensitive unit. The device is applicable to accurate measurement of fluid volumes.

10 Claims, 3 Drawing Sheets

DEVICE FOR MEASURING THE VISCOSITY OF A FLUID

FIELD OF THE INVENTION

The present invention concerns a device for measuring the viscosity of a fluid.

The invention finds a particularly advantageous application in the general field of hydraulics and more particularly in that of accurate measurement of the volume of fluid delivered by a dispenser, in particular a fuel dispenser.

BACKGROUND OF THE INVENTION

Fuel dispensers are equipped with a unit for measuring the volume of fuel dispensed. This unit, also known as a measurer, is generally a volumetric meter and can be either a mechanical device or a static device.

The function of a mechanical measurer is to convert the flow of the fuel into rotary motion in which one complete revolution corresponds to a given volume of fuel passing through the measurer. An optical or magnetic encoding system responsive to the rotary motion supplies an electrical signal made up of a series of pulses each of which corresponds to a volume measurement increment, for example 1 centiliter (cl).

Static measurers have no moving parts. They include ultrasonic measurers and fluidic oscillators.

With some measurers, in particular fluidic oscillators, the resulting volume measurement can be influenced by the viscosity of the fluid, and to be more precise by its Reynolds number, which operates in the form of an error function relative to a main function that is independent of the Reynolds number. This applies in particular to fluidic oscillators, in which the frequency of oscillation is proportional to the flowrate of the fluid to a first approximation. However, a correctional term dependent on Reynolds number must be taken into account if sufficient accuracy is to be achieved.

It should be emphasized that the viscosity of a fluid is not constant, and that it can vary for the same fluid from one shipment to another. In the case of fuel, the viscosity can change during a single dispensing operation because of temperature fluctuations. If sufficient measuring accuracy is to be achieved, it is sometimes essential to know in real time the viscosity or the Reynolds number of the fluid for which the dispensed volume is to be measured, these two magnitudes being proportional.

Various methods are known for measuring the viscosity of a fluid.

The Couette method measures the force mechanically resisting the movement of two plates relative to each other due to the displacement of a thin film of fluid contained between the two plates. The dynamic viscosity $\mu$ of the fluid is directly proportional to the measured resisting force. In practice, the plates are usually in the form of two coaxial cylinders and the viscosity is determined by measuring the torque needed to immobilize one of the two cylinders when the other is rotating at a given speed. That method, which is widely used, has the advantage of allowing continuous measurement. On the other hand, the devices employed are complex and fragile (fine guides, presence of a motor, a torque meter, etc.).

Other methods are based on Poiseuille's law which states that, for laminar flow in a capillary tube, the flowrate and the head loss between the ends of the tube are proportional, the coefficient of proportionality depending on the viscosity of the fluid. There are many devices operating in accordance with that principle. The simplest of them includes a vertical capillary tube having a central enlargement. The viscosity of the fluid is measured by measuring the time required for the fluid to flow under its own weight between two marks at opposite sides of the enlargement. The drawbacks of that type of technique are as follows:

measurement is non-continuous, and can only be effected by periodically taking samples of the fluid, manual intervention is necessary, each tube provides only a small range of measurements. The diameter of the capillary tube is chosen to maintain laminar flow, i.e. a Reynolds number of low value. Because Reynolds number Re is dependent on the dynamic viscosity $\mu$ of the fluid (Re=$4\rho Q/\pi\mu d$ with $\rho$=density of the fluid, Q=flowrate, d=tube diameter), the same tube can be used for only a limited range of viscosities, and capillary tubes of very small diameter can easily become blocked.

Finally, it may be observed that the two methods described hereinabove can only be used at low flowrates Q of less than 1 liter per minute (1/min) if laminar conditions are to be maintained.

OBJECTS AND SUMMARY OF THE INVENTION

An object of the present invention is to measure the viscosity of a fluid in a way that enables simple and continuous measurements to be made over a wide range of flowrates including flowrates of up to several tens of liters per minute.

This and other objects of the invention are attained in accordance with one aspect of the present invention which is directed to a device for measuring the viscosity of a fluid. The device includes a viscosensitive unit through which the fluid flows under laminar flow conditions, a first turbulent flow flowmeter in series with said viscosensitive unit, and a second turbulent flow flowmeter shunting at least the viscosensitive unit. The flowmeters are adapted to determine the head loss $\Delta\Delta p$ and the flowrate q of the fluid through the viscosensitive unit, its dynamic viscosity $\mu$ being given by the equation $\mu=\Delta p/kq$ where k is a constant dependent on the viscosensitive unit.

The device of the invention is based on application of Poiseuille's law to the viscosensitive unit under laminar flow conditions, i.e. $\Delta p=k\mu q$. The head loss $\Delta p$ and the flowrate q are measured by the turbulent flow flowmeters whose characteristics also depend on viscosity $\mu$ but to a much lower degree, which leads to significant errors only for high head losses. The head loss $\Delta p$ across a flowmeter is then a quadratic function of the flowrate Q.

The viscosity measuring device of the invention has a number of advantages over prior art viscosity meters. It allows continuous measurement, and therefore measurement in real time, and it uses simple means, in particular existing flowmeters, that do not require motors or any other complex devices. An appropriate shape and structure of the viscosensitive unit make it possible to obtain laminar flow throughout the ranges of viscosities to be measured and of working flowrates.

Two embodiments of the measuring device of the invention are disclosed. In the first embodiment, the second flowmeter shunts the viscosensitive unit only, and in the second embodiment the second flowmeter shunts both the viscosensitive unit and the first flowmeter. The second embodiment has the advantage of not combining two head losses in series.

BRIEF DESCRIPTION OF THE DRAWING

The following description with reference to the accompanying drawings, which are given by way of non-limiting example, explains the invention and how it can be put into effect.

FIG. 4b is a top view of the viscosensitive unit from FIG. 4a.

DETAILED DESCRIPTION OF THE PREFERRED EMBODIMENTS

Figure 1:
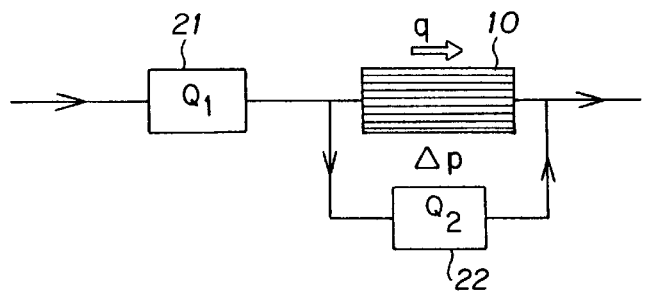
FIG. 1 is a block diagram of a first embodiment of a device in accordance with the invention for measuring the viscosity of a fluid.

FIG. 1 shows a device for measuring the viscosity of a fluid including a viscosensitive unit 10 through which said fluid flows under flow conditions that are laminar in the sense that the head loss $\Delta p$ across the viscosensitive unit 10 and the fluid flowrate q are related by the equation:

$$\Delta p = k \mu q \quad (1)$$

where $\mu$ is the dynamic viscosity of the fluid and k is a constant dependent on the viscosensitive unit.

If the flowrate q is known, measuring the value of the head loss $\Delta p$ gives an indication that is directly proportional to the viscosity to be measured.

From a practical point of view, an accurate measurement of the head loss in dynamic operation is not always easy to obtain, and in a good many hydraulic installations it can be disturbed by the presence of vibration due to pumps or other moving parts. It is therefore preferable, instead of measuring the head loss $\Delta p$, to use it to vary the flowrate of fluid in a branch circuit. The viscosity measurement is then obtained by means of a flowrate measurement.

To be more precise, the parameters $\Delta p$ and q are measured by two turbulent flow flowmeters 21, 22 to obtain a head loss $\Delta p$/flowrate Q relationship for each flowmeter of the type $\Delta p = a\, Q^2$ where a is substantially independent of the viscosity. In the FIG. 1 diagram, the first flowmeter 21 is in series with the viscosensitive unit 10 and the second flowmeter 22 shunts said viscosensitive unit. Under these conditions, $\Delta p$ and q are given by:

$$\Delta p = \Delta P_2 = a_2 Q_2^2$$

$$q = Q_1 - Q_2$$

Replacing $\Delta p$ and q in equation (1) we obtain:

$$a_2 Q_2^2 = k\mu(Q_1 - Q_2)$$

Finally, by setting $x = Q_2/Q_1$ and $Q_t = Q_1$, the expression for the viscosity is:

$$\mu = (a_2/k) x^2 Q_t/(1-x) \quad (2)$$

The viscosity $\mu$ is therefore defined by the ratio $Q_2/Q_1$ and the total flowrate $Q_t$, the coefficient $a_2/k$ being determined by prior calibration.

Of course, the flowmeter 21 could equally well be downstream of the viscosensitive unit 10.

Figure 2:
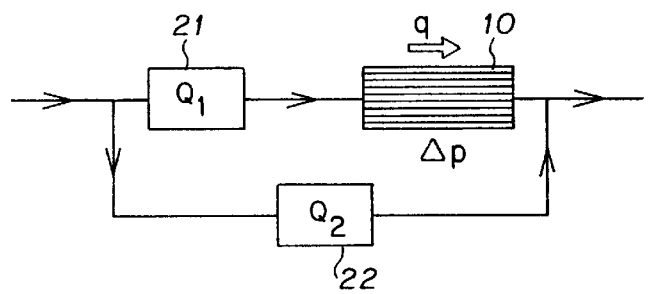
FIG. 2 is a block diagram of a second embodiment of a device in accordance with the invention for measuring the viscosity of a fluid.

In the FIG. 2 embodiment, the second flowmeter 22 shunts the combination of the viscosensitive unit 10 and the first flowmeter 21.

In this case:

$$q = Q_1$$

and $$\Delta p = a_2 Q_2^2 - a_1 Q_1^2$$

Replacing $\Delta p$ and q in equation (1), we obtain:

$$a_2 Q_2^2 - a_1 Q_1^2 = k\mu Q_1$$

Thus with $Qt = Q_1 + Q_2$ = total flowrate and $x = Q_2/Q_1$:

$$\mu = (1/k)(a_2 x^2 - a_1) Qt/(x+1) \quad (3)$$

Once again, the viscosity $\mu$ is expressed as a function of the ratio $Q_2/Q_1$ and the total flowrate $Q_t$, the coefficients $a_1/\mu$ and $a_2/\mu$ being determined by prior calibration.

Note that compared to the arrangement of FIG. 1, that of FIG. 2 has the advantage of not adding head losses in series.

The two measuring devices from FIGS. 1 and 2 lead to the same result, namely the viscosity $\mu$ expressed as a function of the parameter x and the total flowrate Qt. By calibration at various flowrates and with fluids with different known viscosities, it is possible either to make direct use of the analytical functions of x and Qt, corresponding to equations (2) and (3), or to produce a table from which the viscosity of the fluid can be determined in real time at any time from the values of x and Qt.

The mathematical expressions derived above are based on the assumption that the coefficients $a_1$ and $a_2$ of the two flowmeters are independent of viscosity $\mu$. Should it be necessary to take account of variation of these coefficients with viscosity, an expansion of the following type could be used:

$$a_i = c_i \mu^2 + d_i \mu + e_i$$

This leads to a more complex expression for the viscosity $\mu$ without in any way changing the principles of the measurement and the measurement device. The coefficients $c_i$, $d_i$, and $e_i$ are determined by prior calibration.

Figure 3:
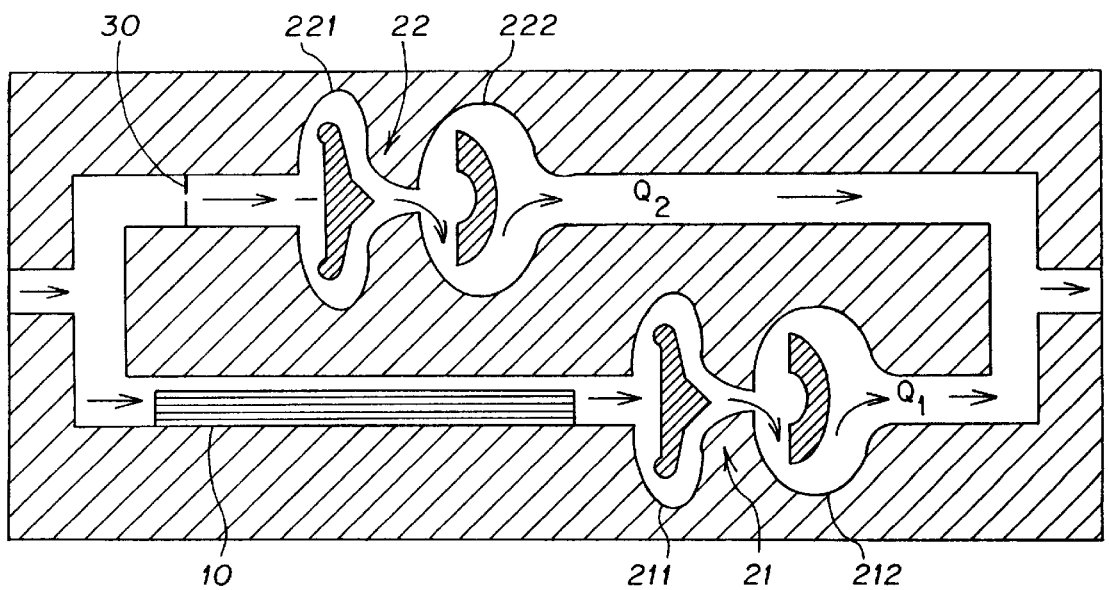
FIG. 3 is a detailed schematic diagram of the embodiment shown in FIG. 2 equipped with fluidic oscillators.

The flowmeters 21, 22 can be mechanical or static volume meters associated with measuring time or frequency. In particular, FIG. 3 shows an embodiment in which the flowmeters 21, 22 are fluidic oscillators, for example identical oscillators. To a first approximation the oscillation frequency F of the jet of fluid in the cavities 212, 222, after shaping in the conditioners 211, 221, is proportional to the flowrate Q. Measuring flowrate therefore amounts to measuring frequency.

As shown in FIG. 3, the two flowmeters 21, 22 and the viscosensitive unit 10 can be incorporated into a single compact block to form a single subassembly.

FIG. 3 also indicates that for balancing the flowrate between the different branches, especially at low flowrates, it may be advantageous to use a flowrate reducing diaphragm 30 to increase the value of the coefficients $a_2$ or $a_1$ as required.

As explained above, the viscosensitive unit 10 must operate under laminar flow conditions, which is the source for the idea of using a capillary tube type profile. However, the small diameter of a capillary tube has the following disadvantages:

low flowrate for a given head loss, high fluid speed, which is incompatible with the required laminar flow conditions (laminar flow is obtained for Reynolds numbers smaller than 2000).

To enable a high throughput while retaining low flow speeds, the viscosensitive unit 10 is a structure made up of n capillary elements connected in parallel, examples of which are shown in FIGS. 4a through 9.

Figure 4A:
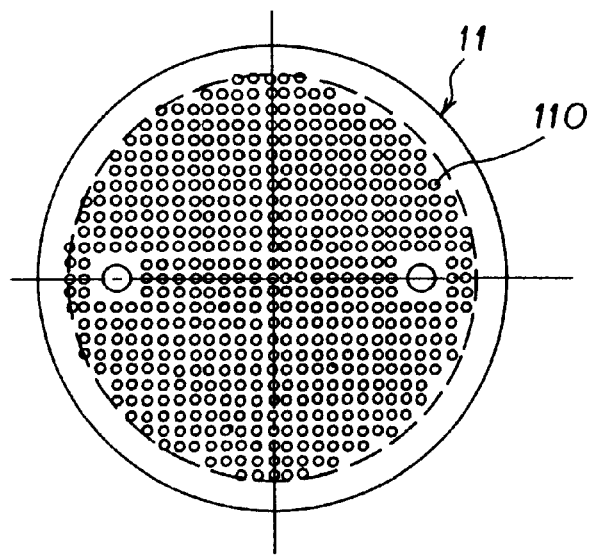
FIG. 4a is a front view of a first embodiment of a viscosensitive unit of the invention.
Figure 4B:
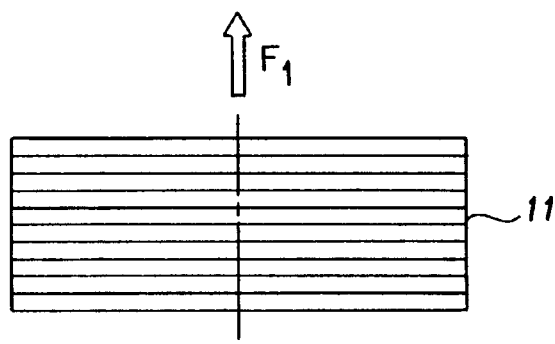

The viscosensitive unit from FIGS. 4a and 4b is equivalent to n tubes in parallel. It is made up of N individual plates 11 each pierced with n holes 110 in a corresponding relationship to form passages parallel to the flow direction $F_1$. The number N of individual plates is chosen to obtain the required length.

Figure 5:
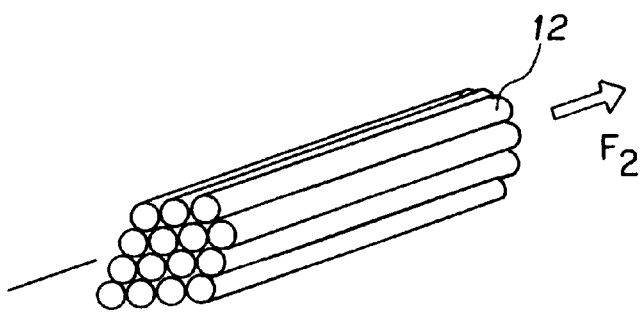
FIG. 5 is a perspective view of a second embodiment of a viscosensitive unit of the invention.

FIG. 5 shows an assembly of n individual tubes 12 parallel to the flow direction $F_2$ grouped together in a compact hexagonal arrangement.

Figure 6:
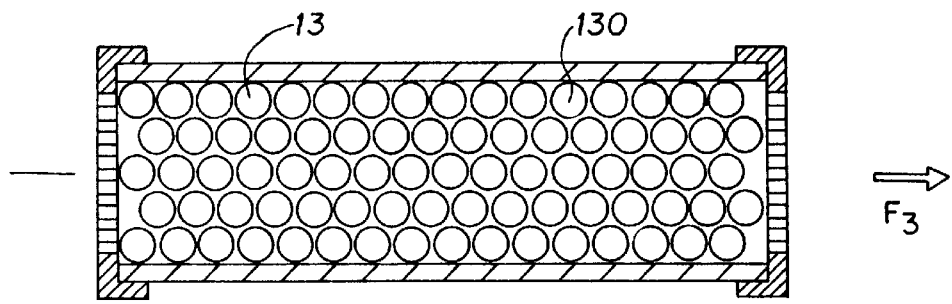
FIG. 6 is a perspective view of a third embodiment of a viscosensitive unit of the invention.

The viscosensitive unit in FIG. 6 is a block of balls 130 held in compression in a housing 13. The flow parallel to $F_3$ is via the interstices between the balls.

Figure 7:
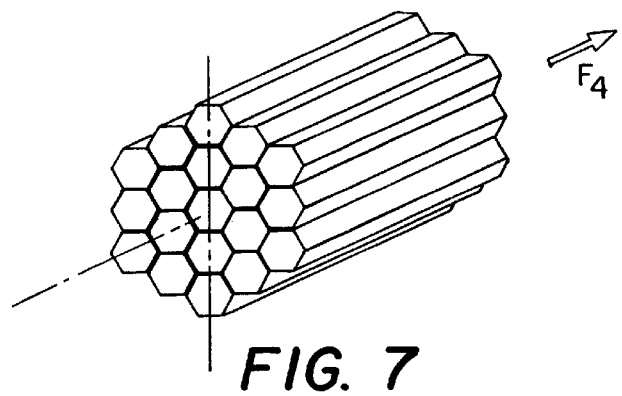
FIG. 7 is a perspective view of a fourth embodiment of a viscosensitive unit of the invention.

The FIG. 7 assembly is equivalent to that of FIG. 5 with a honeycomb structure having a flow direction $F_4$.

Figure 8:
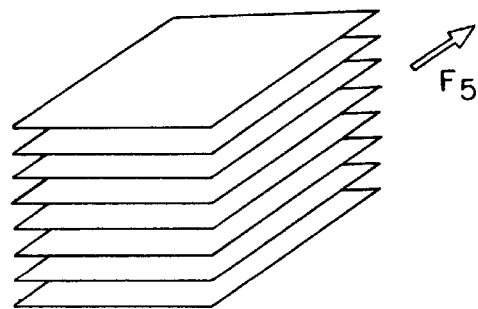
FIG. 8 is a perspective view of a fifth embodiment of a viscosensitive unit of the invention.
Figure 9:
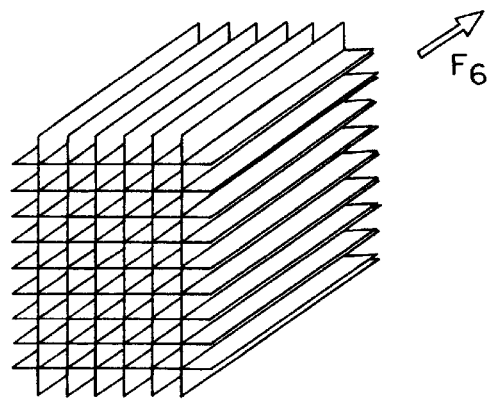
FIG. 9 is a perspective view of a sixth embodiment of a viscosensitive unit of the invention.

FIGS. 8 and 9 show viscosensitive units made from plates parallel to the flow direction $F_5$, $F_6$. The FIG. 8 structure is formed of a single assembly of parallel plates and the FIG. 9 structure has two perpendicular sets of plates forming a grid. The geometrical parameters of these units (flow length, flow cross-section, number of elements in parallel) are defined in accordance with the following parameters:

range of viscosities to be detected, range of operating flowrates, hydraulic characteristics (head loss) of the various parts of the system.

We claim:

1. A device for measuring the viscosity of a fluid wherein said device includes:

a viscosensitive unit through which said fluid flows under laminar flow conditions, a first turbulent flow flowmeter in series with said viscosensitive unit, and a second turbulent flow flowmeter shunting at least the viscosensitive unit, said flowmeters being adapted to determine the head loss $\Delta p$ and the flowrate q of the fluid through the viscosensitive unit, the dynamic viscosity $\mu$ being given by the equation $\mu=\Delta p/kq$ where k is a constant dependent on the viscosensitive unit.

2. A device according to claim 1, wherein the second flowmeter shunts only the viscosensitive unit.

3. A device according to claim 1, wherein the second flow meter shunts both the viscosensitive unit and the first flowmeter.

4. A device according to claim 1, wherein a diaphragm is disposed in series with at least one of the two flowmeters.

5. A device according to claim 1, wherein said flowmeters are volume meters associated with a time measurement.

6. A device according to claim 5, wherein said volume meters are mechanical meters.

7. A device according to claim 5, wherein said volume meters are static meters.

8. A device according to claim 7, wherein said static meters are ultrasonic meters.

9. A device according to claim 7, wherein said static meters are fluidic oscillators.

10. A viscosensitive unit for a device according to claim 1, wherein said viscosensitive unit has a structure made up of n capillary elements in parallel.

* * * * *